United States Patent
Cates et al.

(10) Patent No.: US 11,819,682 B2
(45) Date of Patent: Nov. 21, 2023

(54) IMPLANT TOOL AND IMPROVED ELECTRODE DESIGN FOR MINIMALLY INVASIVE PROCEDURE

(71) Applicant: CVRx, Inc., Minneapolis, MN (US)

(72) Inventors: Adam Cates, Delano, MN (US); Eric Lovett, Mendota Heights, MN (US); Loren Murney, Oak Grove, MN (US); Kip Ludwig, North Bethesda, MD (US); Paul Pignato, Stacy, MN (US); Brian Soltis, St. Paul, MN (US)

(73) Assignee: CVRx, Inc., Minneapolis, MN (US)

( * ) Notice: Subject to any disclaimer, the term of this patent is extended or adjusted under 35 U.S.C. 154(b) by 336 days.

(21) Appl. No.: 17/345,858

(22) Filed: Jun. 11, 2021

(65) Prior Publication Data

US 2021/0308447 A1 Oct. 7, 2021

Related U.S. Application Data

(63) Continuation of application No. 16/438,644, filed on Jun. 12, 2019, now Pat. No. 11,058,869, which is a
(Continued)

(51) Int. Cl.
*A61N 1/36* (2006.01)
*A61N 1/05* (2006.01)

(52) U.S. Cl.
CPC .............. *A61N 1/05* (2013.01); *A61N 1/0558* (2013.01); *A61N 1/3616* (2013.01);
(Continued)

(58) Field of Classification Search
CPC .... A61N 1/05; A61N 1/0558; A61N 1/36117; A61N 1/36139; A61N 1/3616; A61N 1/36171; A61N 1/36175; A61N 1/36182
See application file for complete search history.

(56) References Cited

U.S. PATENT DOCUMENTS 4,058,128 A 11/1977 Frank et al.
4,146,037 A 3/1979 Flynn et al.
(Continued)

FOREIGN PATENT DOCUMENTS

WO WO 94/16766 8/1994
WO WO 2007/075593 A1 7/2007

OTHER PUBLICATIONS

International Preliminary Report on Patentability for PCT Application PCT/US2011/058676, dated May 10, 2013, 5 pgs.
(Continued)

*Primary Examiner* — Amanda K Hulbert
*Assistant Examiner* — Natasha Patel
(74) *Attorney, Agent, or Firm* — Patterson Thuente IP

(57) ABSTRACT

Devices and methods of use for introduction and implantation of an electrode as part of a minimally invasive technique. An implantable baroreflex activation system includes a control system having an implantable housing, an electrical lead, attachable to the control system, and an electrode structure. The electrode structure is near one end of the electrical lead, and includes a monopolar electrode, a backing material having an effective surface area larger than the electrode, and a releasable pivotable interface to mate with an implant tool. The electrode is configured for implantation on an outer surface of a blood vessel and the control system is programmed to deliver a baroreflex therapy via the monopolar electrode to a baroreceptor within a wall of the blood vessel.

7 Claims, 12 Drawing Sheets

Related U.S. Application Data continuation of application No. 15/251,239, filed on Aug. 30, 2016, now Pat. No. 10,350,406, which is a continuation of application No. 14/319,770, filed on Jun. 30, 2014, now Pat. No. 9,511,218, which is a continuation of application No. 13/540,218, filed on Jul. 2, 2012, now Pat. No. 8,788,066, which is a continuation of application No. 13/286,169, filed on Oct. 31, 2011, now Pat. No. 8,437,867.

(60) Provisional application No. 61/515,015, filed on Aug. 4, 2011, provisional application No. 61/408,421, filed on Oct. 29, 2010.

(52) U.S. Cl.
CPC ...... *A61N 1/36117* (2013.01); *A61N 1/36139* (2013.01); *A61N 1/36171* (2013.01); *A61N 1/36175* (2013.01); *A61N 1/36182* (2013.01)

(56) References Cited

U.S. PATENT DOCUMENTS

| | | | |
|---|---|---|---|
| 4,177,818 | A | 12/1979 | De Pedro |
| 4,291,707 | A | 9/1981 | Heilman et al. |
| 4,306,560 | A | 12/1981 | Harris |
| 4,404,971 | A | 9/1983 | LeVeen et al. |
| 4,602,624 | A | 7/1986 | Naples et al. |
| 4,800,879 | A | 1/1989 | Golyakhovsky et al. |
| 4,827,932 | A | 5/1989 | Ideker et al. |
| 4,972,847 | A | 11/1990 | Dutcher et al. |
| 5,154,182 | A | 10/1992 | Moaddeb |
| 5,385,579 | A | 1/1995 | Helland |
| 5,464,447 | A | 11/1995 | Fogarty et al. |
| 5,800,389 | A | 9/1998 | Burney et al. |
| 6,602,241 | B2 | 8/2003 | Makower et al. |
| 6,660,024 | B1 | 12/2003 | Flaherty et al. |
| 6,718,212 | B2 | 4/2004 | Parry et al. |
| 7,369,901 | B1 | 5/2008 | Morgan et al. |
| 7,373,207 | B2 | 5/2008 | Lattouf |
| 8,437,867 | B2 | 5/2013 | Murney et al. |
| 8,788,066 | B2 | 7/2014 | Cates et al. |
| 9,511,218 | B2 | 12/2016 | Cates et al. |
| 10,350,406 | B2 | 7/2019 | Cates et al. |
| 2002/0035378 | A1 | 3/2002 | Bardy et al. |
| 2003/0120264 | A1 | 6/2003 | Lattouf |
| 2004/0015193 | A1 | 1/2004 | Lamson et al. |
| 2005/0004644 | A1 | 1/2005 | Kelsch et al. |
| 2005/0080470 | A1 | 4/2005 | Westlund |
| 2005/0149155 | A1 | 7/2005 | Schelner et al. |
| 2006/0293712 | A1 | 12/2006 | Kieval et al. |
| 2007/0073098 | A1 | 3/2007 | Lenker et al. |
| 2007/0129760 | A1 | 6/2007 | Demarais et al. |
| 2008/0004673 | A1 | 1/2008 | Rossing et al. |
| 2008/0132966 | A1 | 6/2008 | Levin et al. |
| 2008/0161887 | A1* | 7/2008 | Hagen ............ A61N 1/05 607/116 |
| 2008/0172116 | A1 | 7/2008 | Mrva et al. |
| 2009/0030469 | A1 | 1/2009 | Meiry |
| 2009/0069738 | A1 | 3/2009 | Rossing et al. |
| 2009/0143837 | A1 | 6/2009 | Rossing |
| 2009/0270962 | A1 | 10/2009 | Yang et al. |
| 2009/0276025 | A1 | 11/2009 | Burnes et al. |
| 2015/0142011 | A1 | 5/2015 | Cates et al. |
| 2017/0007826 | A1 | 1/2017 | Cates et al. |

OTHER PUBLICATIONS

International Search Report and Written Opinion from PCT Application PCT/US2011/058676, dated May 30, 2012, 8 pgs.

Application and File History for U.S. Appl. No. 13/286,169, filed Oct. 31, 2011, now issued as U.S. Pat. No. 8,437,867, Applicants Murney et al.

Application and File History for U.S. Appl. No. 13/540,218, filed Jul. 2, 2012, now issued as U.S. Pat. No. 8,788,066, Applicants Cates et al.

Application and File History for U.S. Appl. No. 14/319,770, filed Jun. 30, 2014, now issued as U.S. Pat. No. 9,511,218 on Dec. 6, 2016, Applicants Cates et al.

Application and File History for U.S. Appl. No. 15/251,239, filed Aug. 30, 2016, now issued as U.S. Pat. No. 10,350,406 Applicants Cates et al.

Partial European Search Report from EP Application 16184400.6-1666, dated Jan. 2, 2017, 6 pgs.

Extended European Search Report from EP Application 16184400.6, dated Apr. 11, 2017, 9 pgs.

Application and File History for U.S. Appl. No. 16/438,644, filed Jun. 12, 2019, Applicants Cates et al.

Extended European Search Report from related EP Application 11837271.3 dated Aug. 5, 2014, 4 pgs.

English translation of First Office Action from related Chinese Application CN201180052646.9 dated Aug. 5, 2014, 5 pgs.

Office Action from Chinese Application CN 201180052646.9, dated Feb. 25, 2015, 8 pgs.

Patent Examination Report from Australian Application AU2011320117, dated Jun. 24, 2015, 3 pgs.

JP Office Action and English translation from related case JP 2013-536915, dated Jul. 31, 2015, 8 pgs . . . .

\* cited by examiner

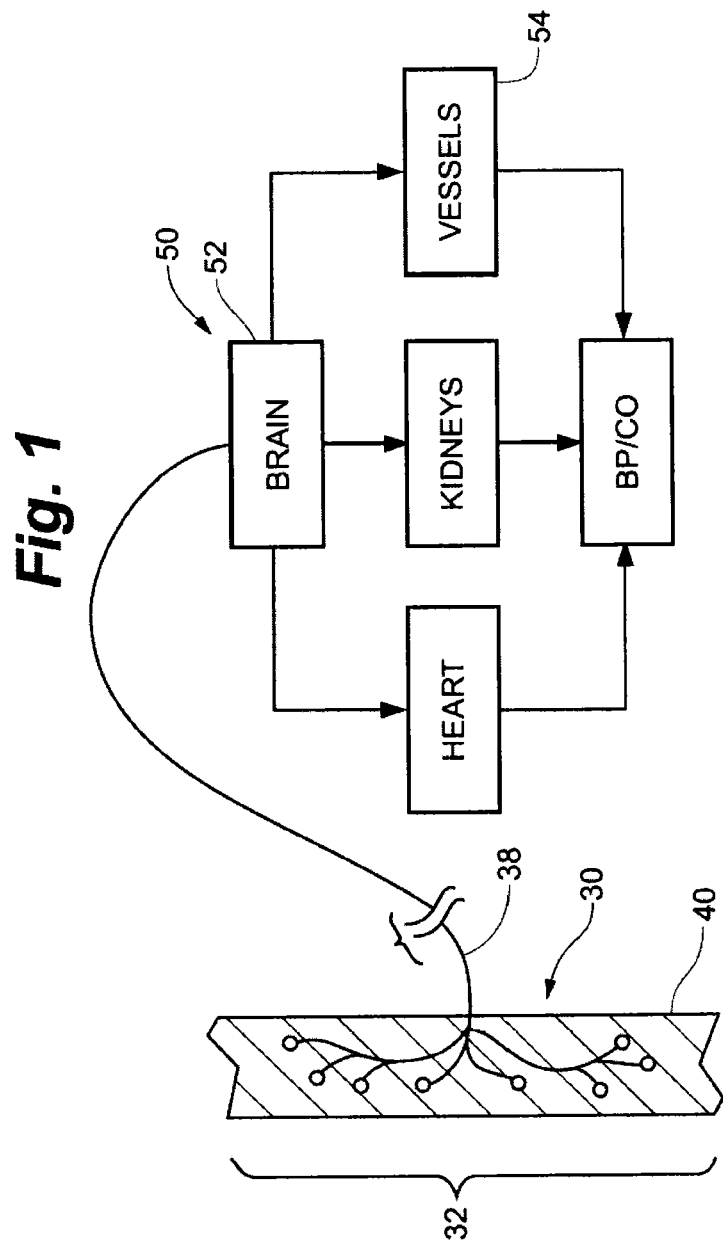

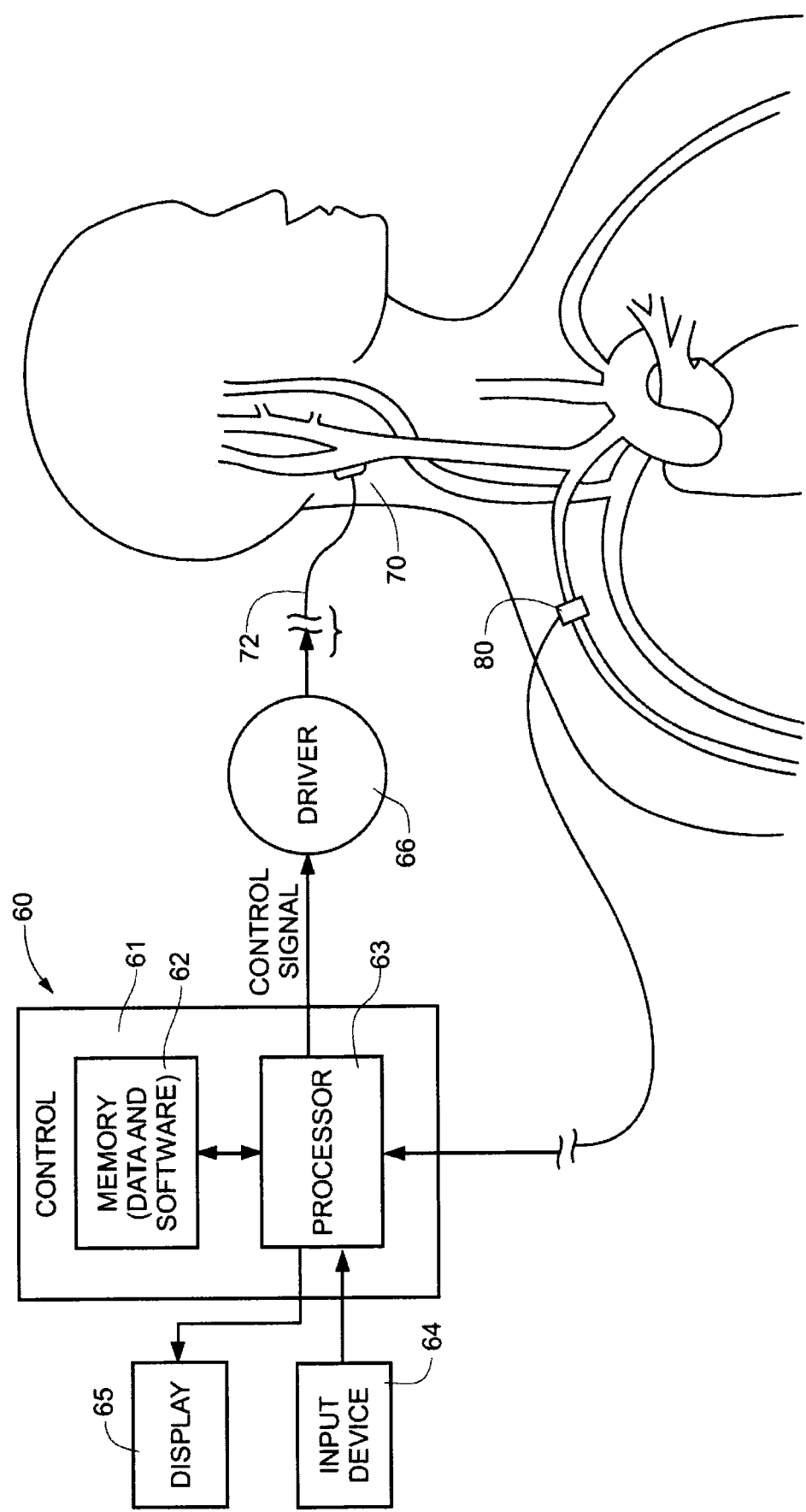

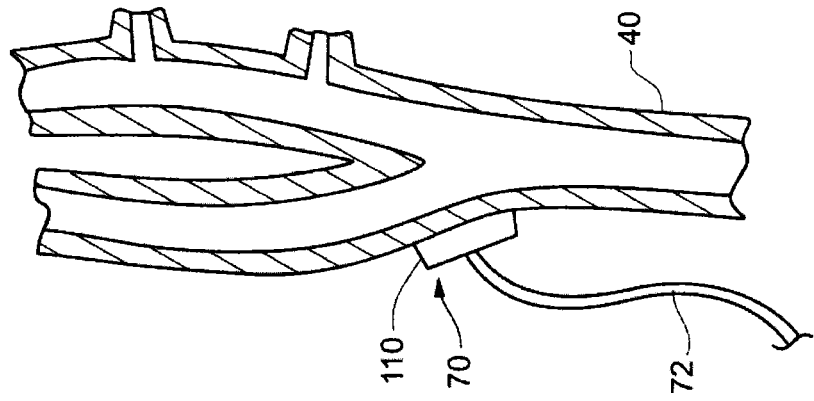
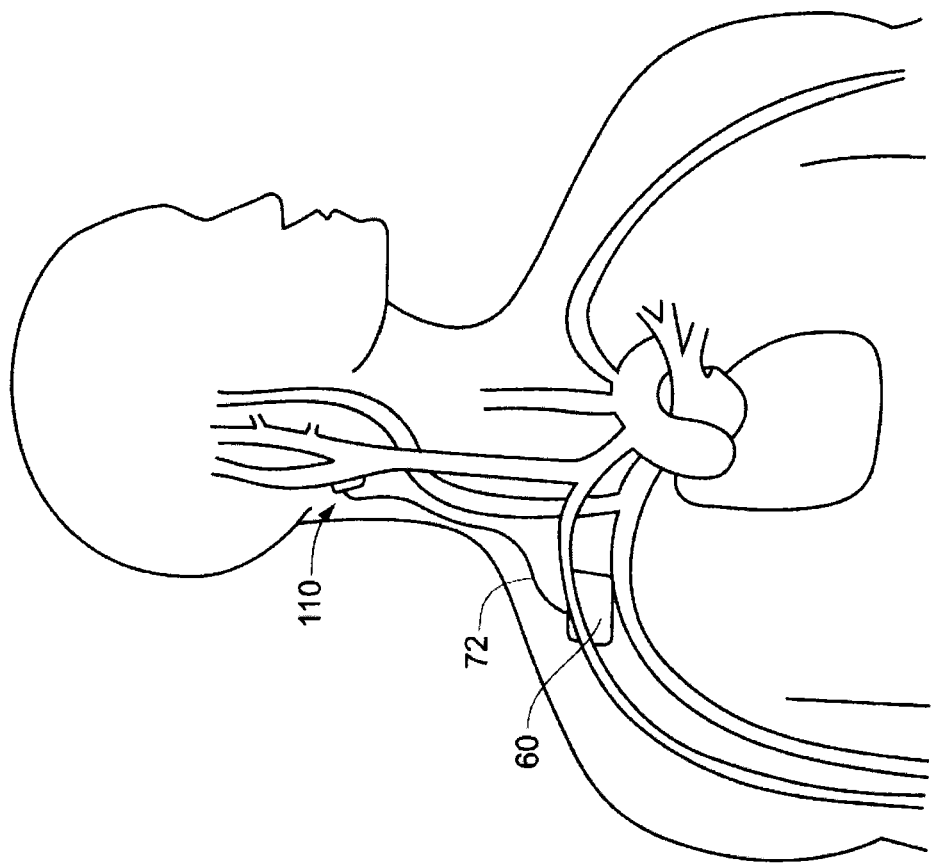

| MONTH | N | AMPLITUDE mA | PULSE WIDTH μs | FREQUENCY Hz |
|---|---|---|---|---|
| 1 | 34 | 5.7 | 122.4 | 46.7 |
| 2 | 28 | 5.9 | 138.1 | 54.8 |
| 3 | 22 | 6.8 | 121.3 | 62.8 |
| 5 | 9 | 6.9 | 118.8 | 64.3 |

IMPLANT TOOL AND IMPROVED ELECTRODE DESIGN FOR MINIMALLY INVASIVE PROCEDURE

CROSS-REFERENCES TO RELATED APPLICATIONS

This application is a continuation of application Ser. No. 16/438,644 filed Jun. 12, 2019, which is a continuation of application Ser. No. 15/251,239 filed Aug. 30, 2016 and now issued as U.S. Pat. No. 10,350,406, which is a continuation of application Ser. No. 14/319,770 filed Jun. 30, 2014 and now issued as U.S. Pat. No. 9,511,218, which is a continuation of application Ser. No. 13/540,218 filed Jul. 2, 2012 and now issued as U.S. Pat. No. 8,788,066, which is a continuation of application Ser. No. 13/286,169, filed Oct. 31, 2011 and now issued as U.S. Pat. No. 8,437,867, which claims the benefit of Provisional Application Nos. 61/408,421, filed Oct. 29, 2010, and 61/515,015, filed Aug. 4, 2011, the disclosures of which are hereby incorporated by reference in their entireties.

FIELD OF THE INVENTION

The present invention relates generally to baroreflex activation therapy devices and methods, and more particularly to an improved electrode design for use with an implant tool and procedure, as part of a baroreflex activation therapy system.

BACKGROUND OF THE INVENTION

Cardiovascular disease is a major contributor to patient illness and mortality. It also is a primary driver of health care expenditure, costing billions of dollars each year in the United States. Heart failure is the final common expression of a variety of cardiovascular disorders, including ischemic heart disease. It is characterized by an inability of the heart to pump enough blood to meet the body's needs and results in fatigue, reduced exercise capacity and poor survival. Heart failure results in the activation of a number of body systems to compensate for the heart's inability to pump sufficient blood. Many of these responses are mediated by an increase in the level of activation of the sympathetic nervous system, as well as by activation of multiple other neurohormonal responses. Generally speaking, this sympathetic nervous system activation signals the heart to increase heart rate and force of contraction to increase the cardiac output; it signals the kidneys to expand the blood volume by retaining sodium and water; and it signals the arterioles to constrict to elevate the blood pressure. The cardiac, renal and vascular responses increase the workload of the heart, further accelerating myocardial damage and exacerbating the heart failure state. Accordingly, it is desirable to reduce the level of sympathetic nervous system activation in order to stop or at least minimize this vicious cycle and thereby treat or manage the heart failure.

Hypertension, or high blood pressure, is a major cardiovascular disorder that is estimated to affect 65 million people in the United States alone. Hypertension occurs when the body's smaller blood vessels (arterioles) constrict, causing an increase in blood pressure. Because the blood vessels constrict, the heart must work harder to maintain blood flow at the higher pressures. Although the body may tolerate short periods of increased blood pressure, sustained hypertension may eventually result in damage to multiple body organs, including the kidneys, brain, eyes and other tissues, causing a variety of maladies associated therewith. The elevated blood pressure may also damage the lining of the blood vessels, accelerating the process of atherosclerosis and increasing the likelihood that a blood clot may develop. This could lead to a heart attack and/or stroke. Sustained high blood pressure may eventually result in an enlarged and damaged heart (hypertrophy), which may lead to heart failure.

Hypertension is a leading cause of heart failure and stroke, is the primary cause of death for tens of thousands of patients per year, and is listed as a primary or contributing cause of death for hundreds of thousands of patients per year in the U.S. Accordingly, hypertension is a serious health problem demanding significant research and development for the treatment thereof. Hypertension remains a significant risk for patients and challenge for health care providers around the world despite improvements in awareness, prevention, treatment and control over the last 30 years. Patients with hypertension are encouraged to implement lifestyle modifications including weight reduction, adopting the DASH eating plan, reducing dietary sodium, increasing physical activity, and limiting alcohol consumption and smoking. A large number of pharmacologic treatments are also currently available to treat hypertension.

An early attempt at treating hypertension first examined in the 1960's and 1970's involved electrically stimulating the carotid sinus nerve. This therapy never gained widespread acceptance, likely due to the simultaneous development of improved pharmacological agents for treating hypertension, limitations associated with battery technology at the time, and surgical limitations relating to isolating and placing electrodes on the carotid sinus nerve. Furthermore, carotid sinus nerve stimulation can negatively affect the patient's breathing patterns as well as blood circulation. The paucity of literature on carotid sinus nerve stimulation during time is reflective of this and the lack of any similar or alternate stimulation systems for the treatment of drug resistant hypertension.

Recently, an improved approach for treating hypertension, heart failure and/or other cardiovascular disorders has been developed. Baroreflex Activation Therapy ("BAT") utilizes electrical, mechanical, chemical, and/or other means of stimulation to activate one or more components of a patient's baroreflex system, such as baroreceptors.

Baroreceptors are sensory nerve ends that are profusely distributed within the arterial walls of the major arteries, as well in the heart, aortic arch, carotid sinus or arteries, and in the low-pressure side of the vasculature such as the pulmonary artery and vena cava. Baroreceptor signals are used to activate a number of body systems which collectively may be referred to as the baroreflex system. Baroreceptors are connected to the brain via the nervous system, allowing the brain to detect changes in blood pressure, which is indicative of cardiac output. If cardiac output is insufficient to meet demand (i.e., the heart is unable to pump sufficient blood), the baroreflex system activates a number of body systems, including the heart, kidneys, vessels, and other organs/tissues. Such natural activation of the baroreflex system generally corresponds to an increase in neurohormonal activity. Specifically, the baroreflex system initiates a neurohormonal sequence that signals the heart to increase heart rate and increase contraction force in order to increase cardiac output, signals the kidneys to increase blood volume by retaining sodium and water, and signals the vessels to constrict to elevate blood pressure. The cardiac, renal and vascular responses increase blood pressure and cardiac output, and thus increase the workload of the heart. In a patient suffering from heart failure, this further accelerates myocardial damage and exacerbates the heart failure state.

One of the first descriptions of treating hypertension through baroreceptor stimulation appears in U.S. Pat. No. 6,522,926 to Kieval et al., which discloses devices and methods for stimulating or activating baroreceptors or the baroreflex system to regulate blood pressure and/or treat other cardiovascular disorders. Generally speaking, a baroreceptor activation device may be activated, deactivated or otherwise modulated to activate one or more baroreceptors and induce a baroreceptor signal or a change in the baroreceptor signal to thereby affect a change in the baroreflex system. The baroreceptor activation device may be activated, deactivated, or otherwise modulated continuously, periodically, or episodically. The baroreceptor activation device may utilize electrical as well as mechanical, thermal, chemical, biological, or a combination thereof to activate the baroreceptor. The baroreceptor may be activated directly, or activated indirectly via the adjacent vascular tissue. Activation of this reflex increases afferent electrical signals through the carotid sinus nerve (Hering's nerve, a branch of the glossopharyngeal nerve, cranial nerve IX) to the medullary brain centers that regulate autonomic tone. Increased afferent signals to these medullary centers cause a reduction in sympathetic tone and an increase in parasympathetic tone. This results in lower heart rate, reduced sodium and water reabsorption by the kidney resulting in a diuresis, relaxation of the smooth muscle in the blood vessels which results in vasodilatation and a reduction in blood pressure. Thus, peripheral activation of the baroreflex results in a physiologic response whereby blood pressure is controlled by mechanisms determined by the integrative action of the central nervous system action on all peripheral organs and blood vessels.

The process of implanting a baroreflex activation device for delivering baroreflex therapy, such as an electrode assembly, involves positioning the assembly such that the electrodes are properly situated against the arterial wall of the carotid sinus, and securing the electrode assembly to the artery so that the positioning is maintained. The process of adjusting and re-adjusting the position of the electrode assembly during implantation, known as mapping, adds to the overall procedure time. Present-day procedures involve positioning and holding the electrode assembly in place with forceps, hemostat or similar tool while applying the stimulus and observing the response in the patient. Movement by as little as 1 mm can make a medically relevant difference in the effectiveness of the baroreceptor activation.

One example of mapping methods and techniques for implanting electrodes is disclosed in U.S. Pat. No. 6,850,801 to Kieval et al. The positioning is a critical step, as the electrodes must direct as much energy as possible toward the baroreceptors for maximum effectiveness and efficiency. The energy source for the implanted baroreflex stimulation device is typically an on-board battery with finite capacity, and it is desirable to provide a lower energy source to ensure patient safety. A high-efficiency implantation will provide a longer battery life and correspondingly longer effective service life between surgeries because less energy will be required to achieve the needed degree of therapy. As such, during implantation of the electrode assembly, the position of the assembly is typically adjusted several times during the implantation procedure in order to optimize the baroreflex response.

Another challenge related to the positioning process is the task of keeping track of previous desirable positions. Because positioning the electrode assembly is an optimization procedure, surgeons will tend to search for better positions until they have exhausted all reasonable alternative positions. Returning the electrode assembly to a previously-observed optimal position can be quite difficult and frustrating, especially under surgical conditions. Additionally, previous mapping approaches required large incisions to provide clearance for positioning and re-positioning of the electrode assembly.

SUMMARY OF THE INVENTION

Devices and methods of use for introduction and implantation of an electrode as part of a minimally invasive technique. An implantable baroreflex activation system includes a control system having an implantable housing, an electrical lead, attachable to the control system, and an electrode structure. The electrode structure is near one end of the electrical lead, and includes a monopolar electrode, a backing material having an effective surface area larger than the electrode, and a releasable pivotable interface to mate with an implant tool. The electrode is configured for implantation on an outer surface of a blood vessel and the control system is programmed to deliver a baroreflex therapy via the monopolar electrode to a baroreceptor within a wall of the blood vessel.

A method of implanting a baroreflex activation system includes creating an incision in a patient and releasably coupling an electrode structure to an implant tool, the electrode structure including a monopolar electrode, a backing material having an effective surface area larger than the monopolar electrode, and a means for releasably and pivotably interfacing with the implant tool. The method further includes determining a suitable implant location for the electrode structure on a blood vessel by manipulating the implant tool within the incision, securing the electrode structure at the implant location such that the monopolar electrode is in contact with an outer surface of the blood vessel, implanting the housing, and connecting the electrode structure to the control system with the electrical lead.

BRIEF DESCRIPTION OF THE DRAWINGS

The invention may be more completely understood in consideration of the following detailed description of various embodiments of the invention in connection with the accompanying drawings, in which:

FIG. 1 is a cross-sectional schematic illustration of baroreceptors within the vascular wall and the baroreflex system.

FIG. 2 is a schematic illustration of a baroreceptor activation system in accordance with the present invention.

FIGS. 8A and 8B are a schematic representations of a baroreflex activation system according to an embodiment of the present invention implanted on a carotid sinus within a patient.

Figure 3A:
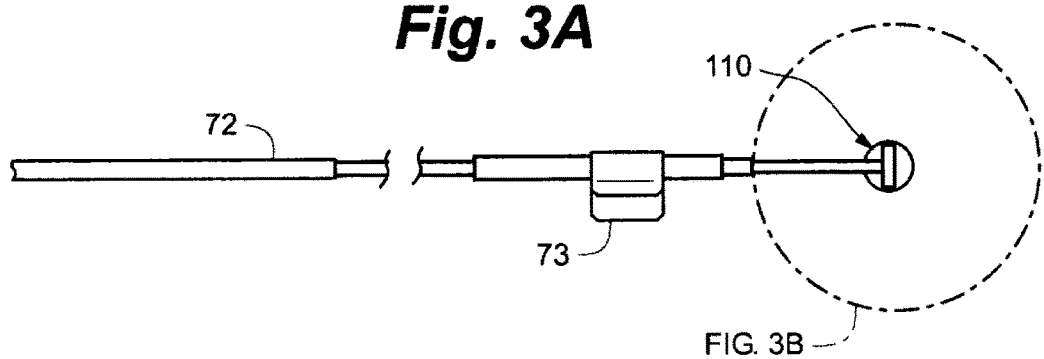
FIG. 3A is a plan view of an electrode coupled with a lead according to an embodiment of the present invention.
Figure 3B:
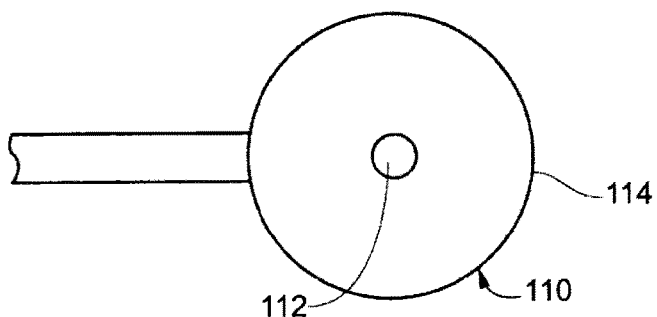
FIG. 3B is a close-up inverted view of a portion of FIG. 3A.
Figure 4A:
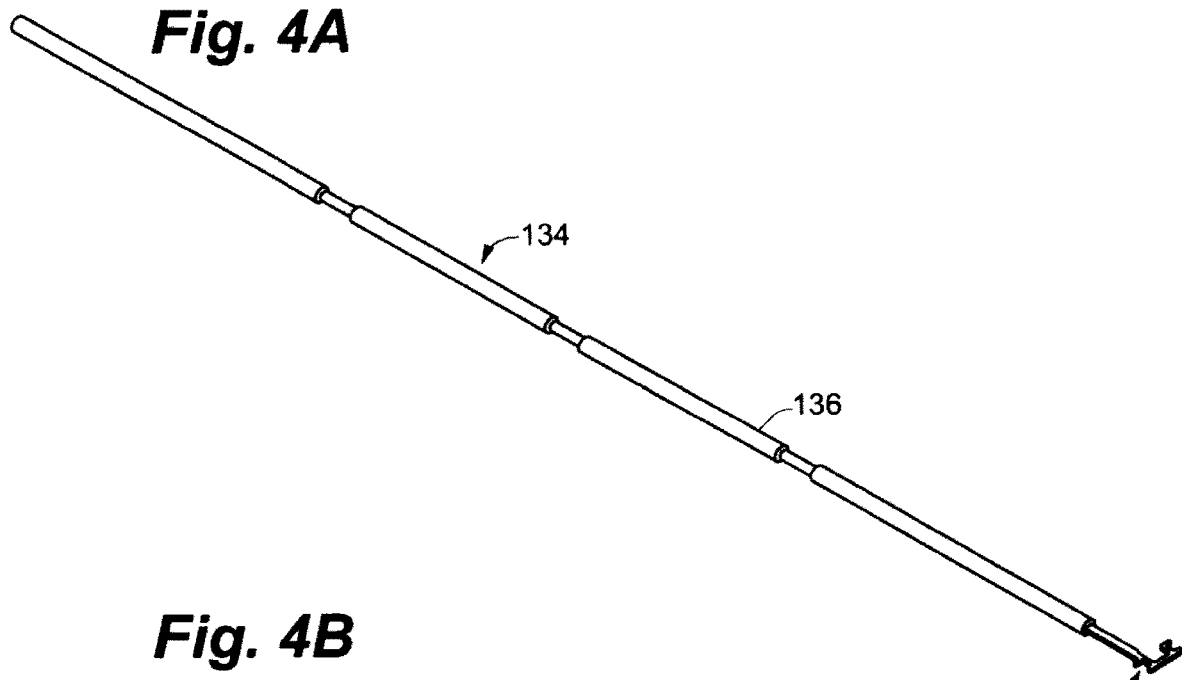
FIG. 4A is an isometric view of an implant tool according to an embodiment of the present invention.
Figure 4B:
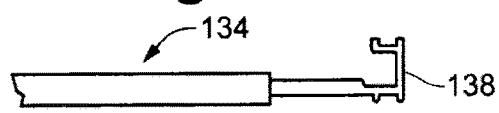
FIG. 4B is a close-up plan view of the interface tip of the implant tool of FIG. 4A.
Figure 4C:
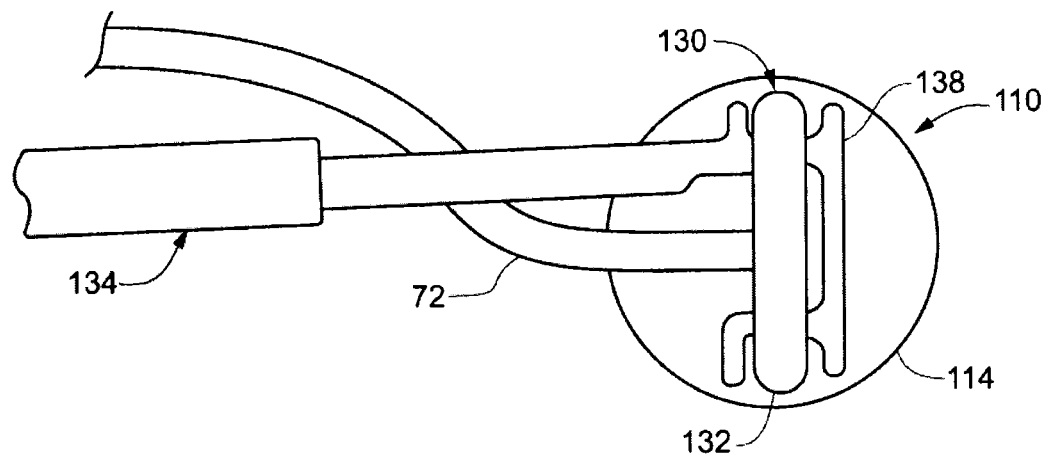
FIG. 4C is a close-up plan view of the implant tool of FIG. 4A coupled with an electrode.
Figure 5A:
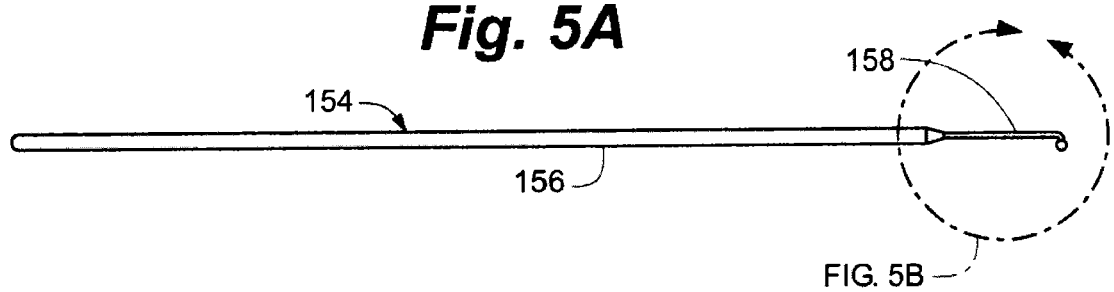
FIG. 5A is an elevation view of an implant tool according to another embodiment of the present invention.
Figure 5B:
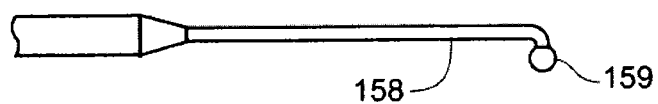
FIG. 5B is a close-up elevation view of a portion of FIG. 5A.
Figure 6A:
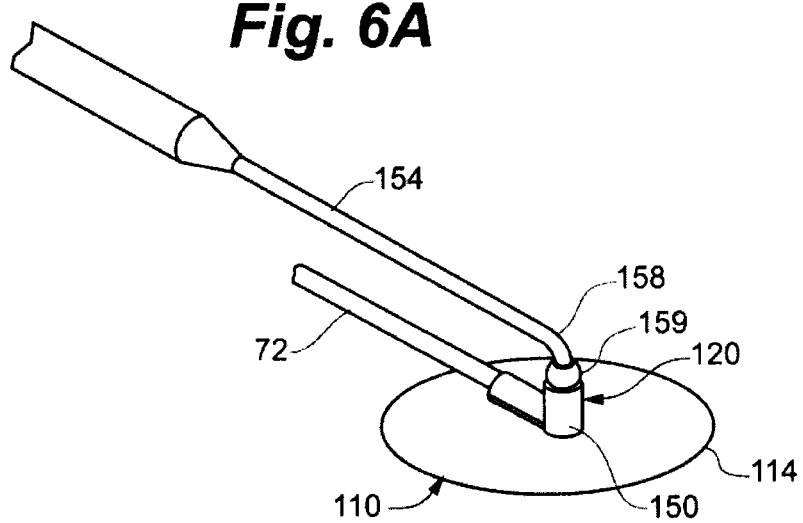
FIG. 6A is an isometric view of the implant tool of FIG. 5A positioned proximate an electrode structure according to an embodiment of the present invention.
Figure 6B:
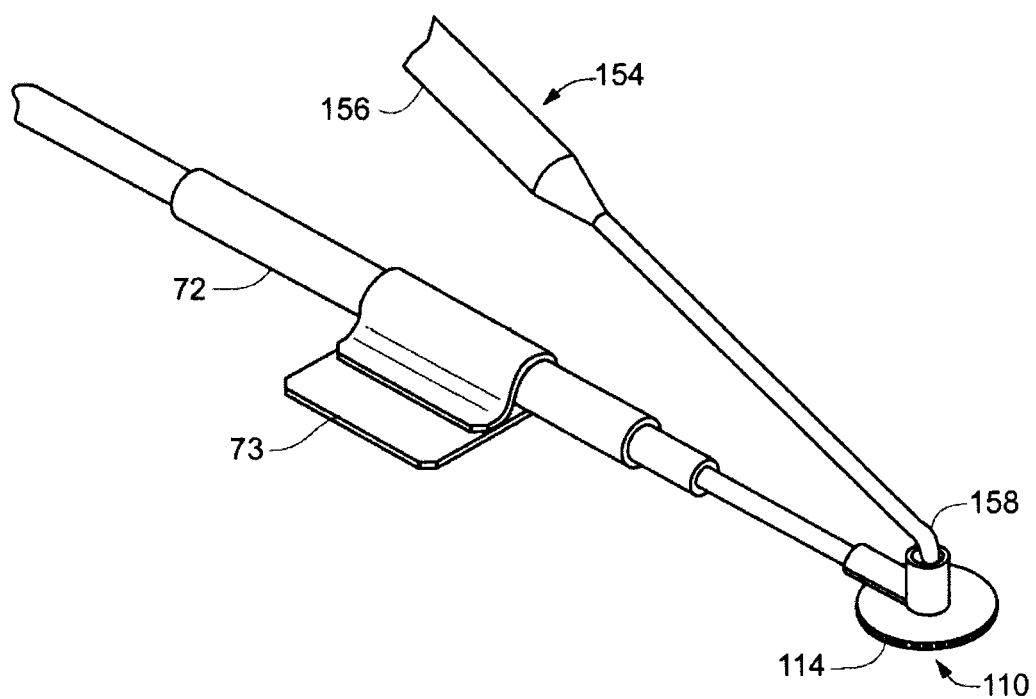
FIG. 6B is an isometric view of the implant tool of FIG. 6A engaged with the electrode structure.
Figure 7A:
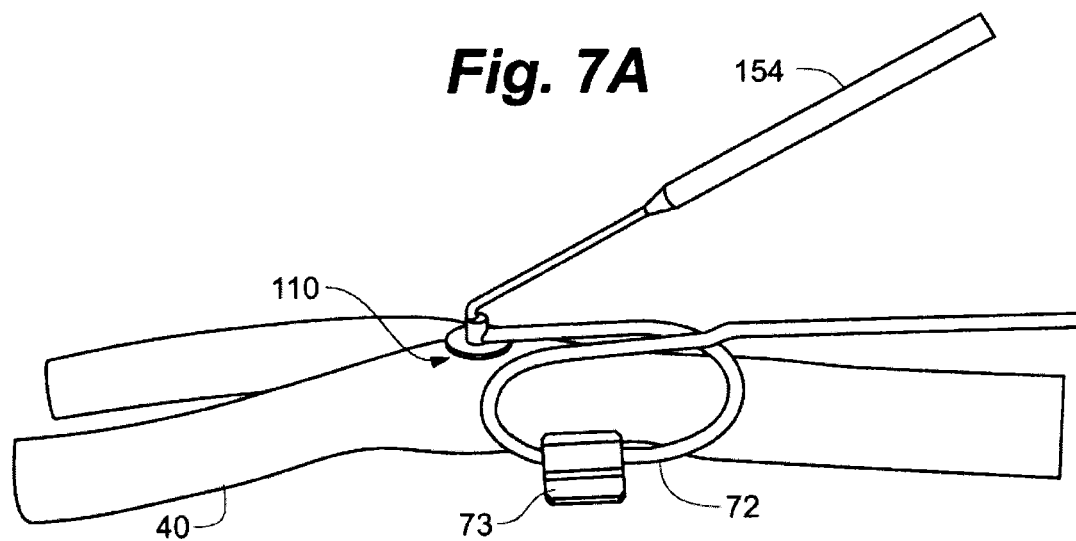
FIG. 7A is a schematic representation of an electrode structure being implanted on a blood vessel with the use of an implant tool, according to an embodiment of the present invention.
Figure 7B:
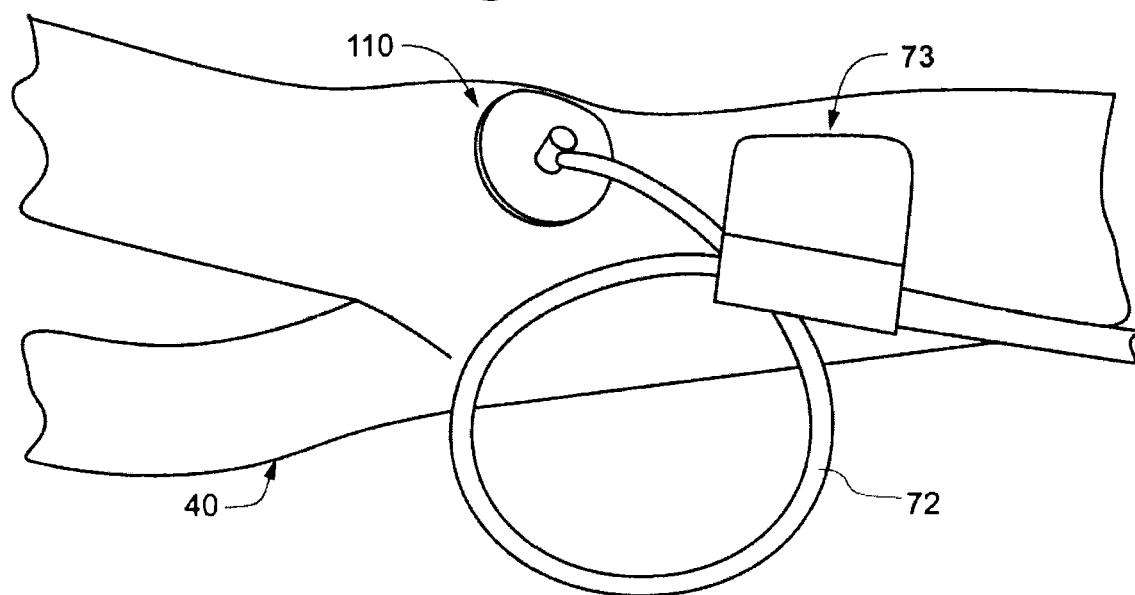
FIG. 7B is a schematic representation of the electrode structure of FIG. 7A fixed in place on the blood vessel.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE DRAWINGS

The following detailed description should be read with reference to the drawings in which similar elements in different drawings are numbered the same. The drawings, which are not necessarily to scale, depict illustrative embodiments and are not intended to limit the scope of the invention.

To address the problems of hypertension, heart failure, other cardiovascular disorders and renal disorders, the present invention basically provides a number of devices, systems and methods by which the baroreflex system is activated to reduce excessive blood pressure, autonomic nervous system activity and neurohormonal activation. In particular, the present invention provides a number of devices, systems and methods by which baroreceptors may be activated, thereby indicating an increase in blood pressure and signaling the brain to reduce the body's blood pressure and level of sympathetic nervous system and neurohormonal activation, and increase parasympathetic nervous system activation, thus having a beneficial effect on the cardiovascular system and other body systems.

For general information pertaining to the cardiovascular, circulatory and nervous systems, as well as baroreceptor and baroreflex therapy systems that may be used in whole or in part with embodiments of the present invention, reference is made to the following commonly assigned patent applications and patents: Published U.S. Patent Application No. 2006/0004417 to Rossing et al. and 2006/0074453 to Kieval et al., and U.S. Pat. No. 6,522,926 to Kieval et al., U.S. Pat. No. 6,850,801 to Kieval et al., U.S. Pat. No. 6,985,774 to Kieval et al., U.S. Pat. No. 7,480,532 to Kieval et al., U.S. Pat. No. 7,499,747 to Kieval et al., U.S. Pat. No. 7,835,797 to Rossing et al., U.S. Pat. No. 7,840,271 to Kieval et al., U.S. Pat. No. 8,086,314 to Kieval, U.S. Pat. No. 8,620,422 to Kieval et al., the disclosures of which are hereby incorporated by reference in their entireties except for the claims and any express definitions.

Refer now to FIG. 1, which depicts a schematic illustration of baroreceptors 30 disposed in a generic vascular wall 40 and a schematic flow chart of the baroreflex system 50. Baroreceptors 30 are profusely distributed within the vascular walls discussed previously, and generally form an arbor 32. The baroreceptor arbor 32 comprises a plurality of baroreceptors 30, each of which transmits baroreceptor signals to the brain 52 via nerve 38. The baroreceptors 30 are so profusely distributed and arborized within the vascular wall 40 that discrete baroreceptor arbors 32 are not readily discernable. To this end, those skilled in the art will appreciate that the baroreceptors 30 depicted in FIG. 1 are primarily schematic for purposes of illustration and discussion.

Baroreceptor signals in the arterial vasculature are used to activate a number of body systems which collectively may be referred to as the baroreflex system. For the purposes of the present invention, it will be assumed that the "receptors" in the venous and cardiopulmonary vasculature and heart chambers function analogously to the baroreceptors in the arterial vasculature, but such assumption is not intended to limit the present invention in any way. In particular, the methods described herein will function and achieve at least some of the stated therapeutic objectives regardless of the precise and actual mechanism responsible for the result. Moreover, the present invention may activate baroreceptors, mechanoreceptors, pressoreceptors, stretch receptors, chemoreceptors, or any other venous, heart, or cardiopulmonary receptors which affect the blood pressure, nervous system activity, and neurohormonal activity in a manner analogous to baroreceptors in the arterial vasculation. For convenience, all such venous receptors will be referred to collectively herein as "baroreceptors" or "receptors" unless otherwise expressly noted.

While there may be small structural or anatomical differences among various receptors in the vasculature, for the purposes of some embodiments of the present invention, activation may be directed at any of these receptors and/or nerves and/or nerve endings from these receptors so long as they provide the desired effects. In particular, such receptors will provide afferent signals, i.e., signals to the brain, which provide the blood pressure and/or volume information to the brain. This allows the brain to cause "reflex" changes in the autonomic nervous system, which in turn modulate organ activity to maintain desired hemodynamics and organ perfusion. Stimulation of the baroreflex system may be accomplished by stimulating such receptors, nerves, nerve fibers, or nerve endings, or any combination thereof.

A baroreflex activation therapy system utilizing an improved electrode and lead arrangement according to embodiments of the present invention generally include a control system, a baroreceptor activation device, a lead and a sensor (optional). Referring now to FIG. 2, one embodiment of a system for baroreflex therapy is depicted, including a control system 60, a baroreflex activation device 70, and one or more sensor(s) 80. The control system 60 may include a therapy block 61 comprising a processor 63 and a memory 62. Control system 60 is enclosed within a housing, or can, and is communicably coupled to baroreflex activation device 70 such as by way of electric control cable 72, or by wireless means such as radiofrequency or other forms of wireless communication. Cable 72 may include an optional attachment tab 73, which may be used to suture or otherwise attach cable 72 to a patient in order to provide strain relief to the electrode-tissue interface. Control system 60 includes a driver 66 to provide the desired power mode for the baroreceptor activation device 70. For example if the baroreceptor activation device 70 utilizes electrical actuation, the driver 66 may comprise a power amplifier, pulse generator or the like to selectively deliver electrical control signals, and the cable 72 may comprise electrical lead(s).

The electrical control signal generated by the driver 66 may be continuous, periodic, episodic or a combination thereof, as dictated by an algorithm contained in memory 62 of the control system 60. Continuous control signals include a constant pulse, a constant train of pulses, a triggered pulse and a triggered train of pulses. Periodic control signals include each of the continuous control signals described above which have a designated start time and a designated duration. Episodic control signals include each of the continuous control signals described above which are triggered by an episode.

The control system memory 62 may contain data related to the sensor signal, the therapy signal, and/or values and commands provided by the input device 64. The memory 62 may also include software containing one or more algorithms defining one or more functions or relationships between the therapy signal and the sensor signal. The algorithm may dictate activation or deactivation therapy signals depending on the sensor signal or a mathematical derivative thereof. The algorithm may dictate an activation or deactivation therapy signal when the sensor signal falls below a lower predetermined threshold value, rises above an upper predetermined threshold value or when the sensor signal indicates a specific physiologic event. The memory 62 may also include software containing one or more algorithms for determining patient physiological parameters based on a measured parameter.

In one embodiment, the sensor(s) 80 senses and/or monitors a parameter, and generates a signal indicative of the parameter. The parameter may be related to cardiovascular function, and/or indicative of a need to modify the baroreflex system, and/or a physical parameter such as vascular impedance. The control system 60 receives the sensor signal from sensor 80 and transmits the therapy signal to the baroreflex activation device 70 by way of control cable 72. The sensor 80 may be combined and/or integrated with baroreflex activation device 70, e.g., an electrode having sensing and therapy capabilities, or sensor 80 may be separate from baroreflex activation device 70 and communicably coupled to control system 60.

The control system 60 generates a control signal (also referred to as a therapy signal), which activates, deactivates or otherwise modulates the baroreflex activation device 70. In one embodiment, the therapy signal is in the range of about 1 to 10 volts, at a rate between 5 Hz and 200 Hz. Typically, activation of the device 70 results in activation of the baroreceptors 30. Alternatively, deactivation or modulation of the baroreflex activation device 70 may cause or modify activation of the baroreceptors 30. The baroreflex activation device 70 may include a wide variety of devices which utilize electrical means, such as electrodes, to activate baroreceptors 30.

The control system 60 may operate as a closed loop utilizing feedback from the sensor 80, and optionally other sensors, such as heart rate sensors, which may be incorporated, or as an open loop utilizing reprogramming commands received by input device 64. The closed loop operation of the control system 60 preferably utilizes some feedback from the sensor(s), but may also operate in an open loop mode without feedback. In a closed loop embodiment, control system 60 generates a control signal as a function of the signal received from sensor 80. Thus, in one embodiment when sensor 80 detects a parameter indicative of the need to modify the baroreflex system activity (e.g., excessive blood pressure), the control system 60 generates a therapy signal to modulate (e.g., activate) the baroreflex activation device 70 thereby inducing a baroreceptor 30 signal that is perceived by the brain 52 to be apparent excessive blood pressure. When the sensor 80 detects a parameter indicative of normal body function (e.g., normal blood pressure), the control system 60 generates a therapy signal to modulate (e.g., deactivate) the baroreflex activation device 70. Programming commands received by the input device 64 may directly influence the therapy signal, the output activation parameters, or may alter the software and related algorithms contained in memory 62. The treating physician and/or patient may provide commands to input device 64. In one embodiment, a display 65 may be used to view the sensor signal, therapy signal and/or the software/data contained in memory 62. Control system 60 may be implanted in whole or in part.

In one embodiment, baroreceptor activation device 70 comprises an electrode structure 110. Electrode structure 110 generally includes an electrode 112 mounted on, integrated with, or otherwise coupled to a backer 114. Electrode 112 may comprise platinum iridium, and may include a surface treatment, such as iridium oxide or titanium nitride and/or can include steroid, anti-inflammatory, antibiotic and/or analgesic compounds, for example. Backer 114 may be constructed of Dacron-reinforced insulated silicone, or other suitable materials that are flexible, sturdy, electrically insulative and/or suitable for implantation in a body. Backer 114 and/or electrode 112 may comprise circular structures, or other suitable arrangements without departing from the spirit of the invention. For example backer 114 may include one or more tabs or features configured for facilitating fixation to tissue. In one embodiment, electrode 112 may have a diameter of about 1 mm, and backer 114 may have a diameter of about 6 mm. However, it is contemplated that electrode 112 may have a diameter within a range of about 0.25 mm-3 mm, while backer 114 may have a diameter within a range of about 1 mm-10 mm. In one embodiment the diameter of backer 114 is at least twice the diameter of electrode 112.

Electrode 112 comprises a cathode, and in one embodiment the housing of control system 60 may comprise an anode. In another embodiment, an anode may be provided as part of lead 72. In another embodiment, an anode is provided on a second lead which is also coupled to control system 60. In all embodiments the anode is preferably sufficiently larger than the cathode, for example ten times larger. In another embodiment the anode is fifty times larger than the cathode. Further, the anode and cathode are preferably positioned at a minimum distance away from one another, for example, the distance may be about twenty times the cathode diameter. In another embodiment, the distance between anode and cathode is at least fifty times the cathode diameter. One or more electrode structures 110 may be provided as part of a baroreflex activation therapy system according to the present invention. For example, a first electrode structure 110 may be positioned at a first anatomical location, while a second electrode structure 110 is positioned at a second anatomical location, such as for example at a left carotid sinus and a right carotid sinus. Or a first electrode structure 110 may be positioned at a first anatomical location while a second electrode structure is positioned at a second anatomical location proximate the first anatomical location, such as for example positioning first and second electrode structures proximate one another on the left carotid sinus and/or carotid arteries.

Electrode structure 110 may also include an interface means 120 configured for coupling with an implant tool, and one or more fixation means 122. Preferably interface means 120 is included on the inactive side of electrode structure 110. As described herein, interface means (or attachment interface) may comprise a t-bar, a socket, or other structure capable of being coupled to or grasped by an implant tool. Referring now to FIGS. 3A-4C, electrode structure 110 includes an interface means 120 in the form of t-bar 130 which includes a bar portion 132 raised above the inactive side of electrode structure 110. T-bar 130 is configured to interface with an implant tool 134, which generally includes a body portion 136 and an interface tip 138. Body portion 136 of tool 134 may be generally rigid, or may include an internal wire or coil to allow tool 134 to be bent or curved and retain the curved shape. Body portion 136 may also include a telescoping or similar arrangement to provide adjustability of the overall length of tool 134. Interface tip 138 may similarly include a telescoping or similar arrangement, separate from that of the body portion. One or more pivot points may also be provided on tool 134, such as between tip 138 and body portion 136, or at any desired location along body 136. Tip portion 138 includes a cradle 139 configured to releasably couple to t-bar 130, while allowing tool 134 to pivot, rotate, and/or otherwise provide freedom of movement about t-bar 130 to facilitate moving electrode structure 110 around the curved surface of an implant location such as the outer surface of a blood vessel 40, as part of a mapping and/or implant procedure.

In another embodiment depicted in FIGS. 5A-7A, interface means 120 comprises a socket 150 disposed on the inactive side of electrode structure 110. Socket 150 is configured to interface with an implant tool 154, which generally includes a body portion 156 and an interface tip 158. Body portion 156 of tool 154 may be generally rigid, or may include an internal coil or wire to allow tool 154 to be bent or curved and retain the curved shape. Body portion 156 may also include a telescoping or similar arrangement to provide adjustability of the overall length of tool 154. Interface tip 158 may similarly include a telescoping or similar arrangement, separate from that of the body portion. One or more pivot points may also be provided on tool 154, such as between tip 158 and body portion 156, or at any desired location along body 156. Tip portion 158 includes a ball end 159 configured to releasably couple to socket 150 of electrode structure 110. The ball-and-socket arrangement provides a wide range of motion about multiple axes between electrode structure 110 and implant tool 154 to facilitate moving electrode structure 110 around the curved surface of an implant location such as the outer surface of a blood vessel 40, as part of a mapping and/or implant procedure. This articulated ball-and-socket joint preferably provides at least three degrees of freedom: pitch, yaw and roll. Further, the ball-and-socket joint preferably provides a range of motion of up to 150 degrees in at least two separate axes.

In order to implant electrode structure 110, a surgeon first identifies and marks the desired implant location. Without limitation, one example of a suitable site for delivering baroreflex activation therapy is the carotid sinus. The general implant location may be obtained with the use of ultrasound, or other imaging techniques known and available. A small incision is made on the patient in the identified region. The length of the incision should be less than four inches long, preferably less than two inches. The size of the incision needed will be determined by the location of the implant and the specific patient, however the electrode structure 110 and implant tool embodiments described herein allow for the use of a minimally invasive incision as compared to implant procedures for previous baroreflex activation devices.

Determining an optimal location to affix electrode structure 110 is critical for effective therapy, and a mapping procedure is therefore undertaken. Electrode structure 110 is releasably coupled to the implant tool, and introduced into the incision until electrode structure 110 is in contact with the implant site, such as for example the carotid sinus. A stimulation signal is provided to electrode structure 110, such as from an external pulse generator, and one or more patient responses to the signal is then measured. Using the implant tool, electrode structure 110 is moved around the contours of the carotid sinus to different positions, with additional stimulation signals delivered and patient responses measured at each position. When the surgeon has located an optimal site for implantation, electrode structure 110 is fixed at the site. The implant tool is then removed.

A path may be tunneled for lead 72 from the electrode implant location to the implant location of control system 60 housing. This path may be tunneled either before or after the mapping procedure. If lead 72 includes a strain relief attachment tab 73, the tab is then sutured in place near electrode structure 110. The control system housing is then implanted subcutaneously as known in the art, and the lead is attached. FIGS. 8A-8B are schematic illustrations of the baroreflex activation system fully implanted.

Figure 9A:
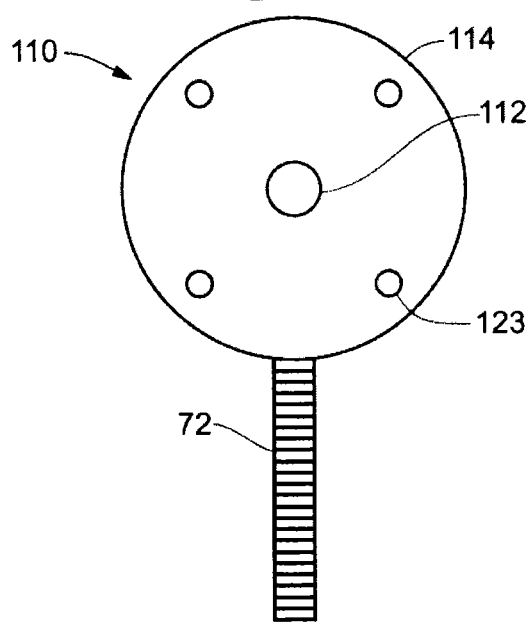
FIG. 9A is a plan view of the tissue contact side of an electrode structure according to an embodiment of the present invention.

Numerous fixation means and techniques are provided for securing electrode structure 110 to an implant site, and may include passive or active fixation. Electrode structure 110 may be sutured directly to a blood vessel, and backer 114 may optionally include one or more apertures 123 as depicted in FIG. 9A, to facilitate a path for sutures through backer 114. Preferably at least two sutures are utilized to insure electrode structure 110 is secure and in sufficient electrical contact with the blood vessel.

Figure 9B:
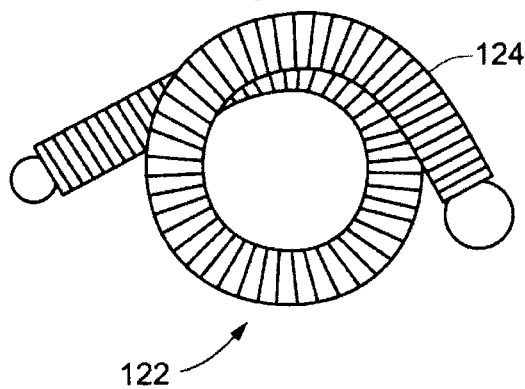
FIG. 9B is a perspective view of a fixation member according to an embodiment of the present invention.
Figure 10A:
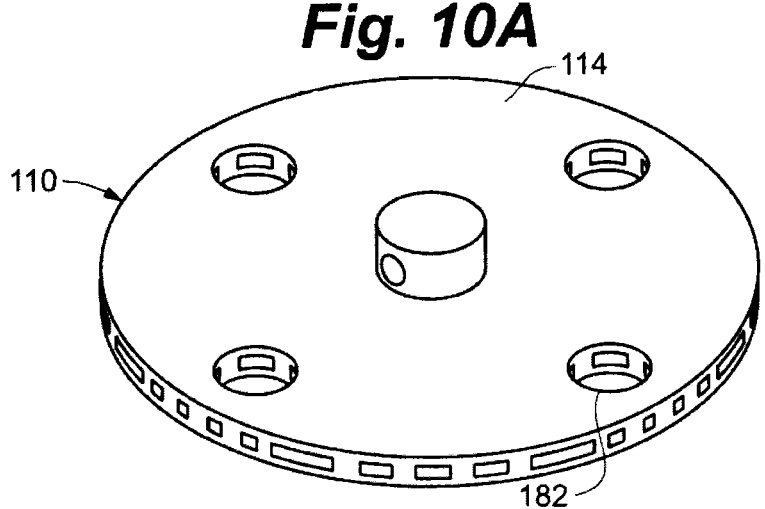
FIGS. 10A-10E are perspective views of related electrode structure configurations according to embodiments of the present invention.
Figure 10B:
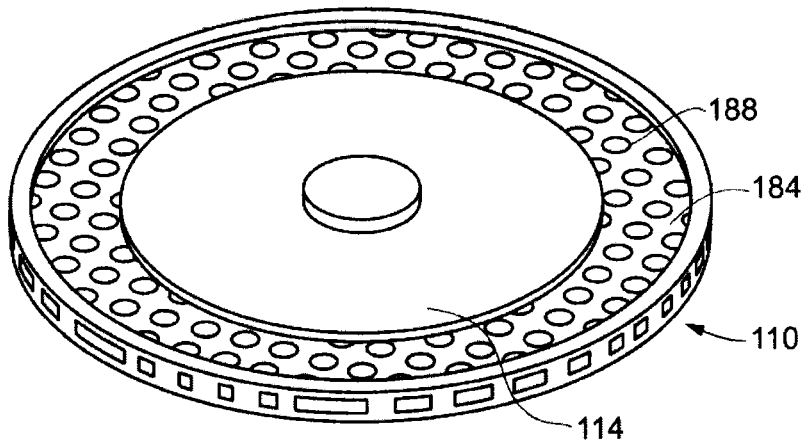
Figure 10C:
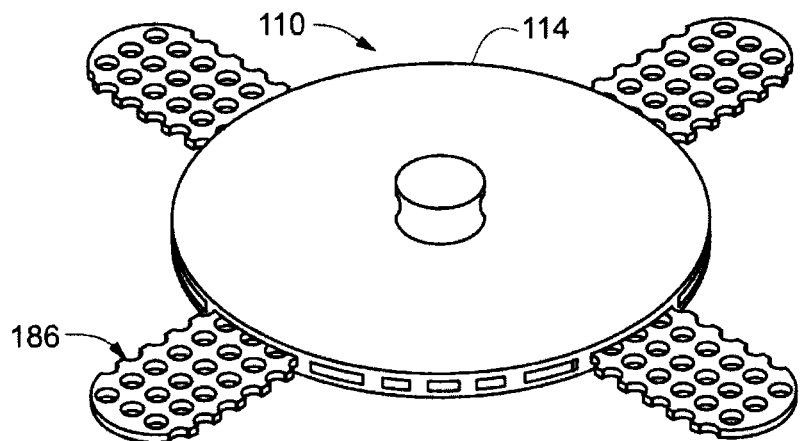
Figure 10D:
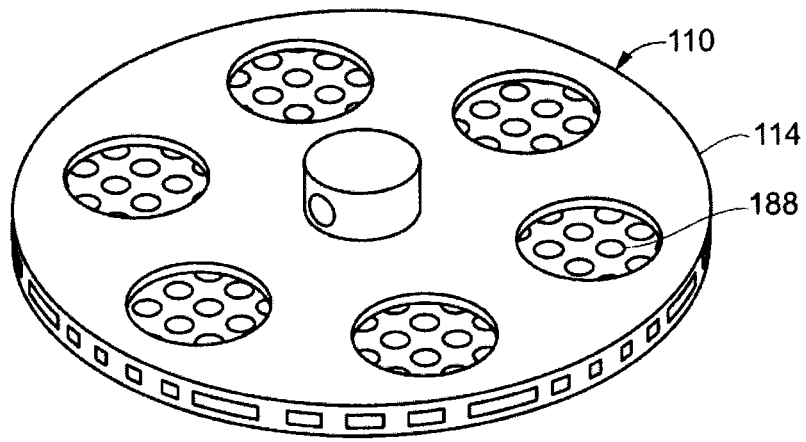
Figure 10E:
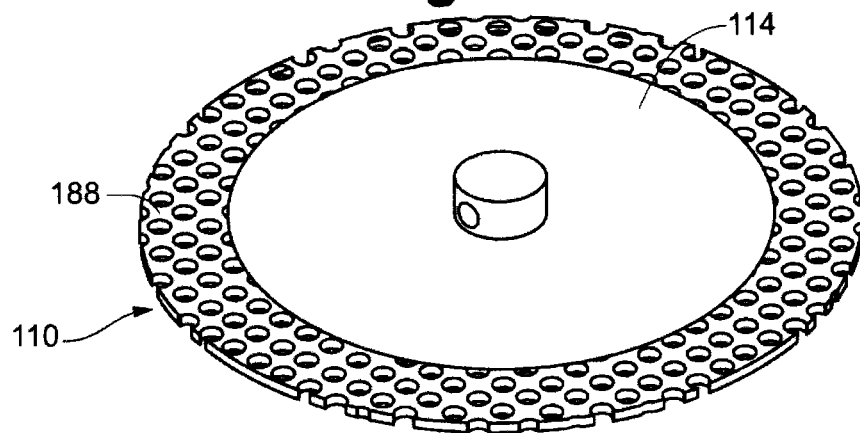

Another embodiment of a fixation means 122 for electrode structure 110, depicted in FIG. 9B, is a U-Clip technique utilizing self-closing nitinol U-Clip components. U-clips 124 (such as those produced by Medtronic, Inc. of Minneapolis, Minn.) can be used to secure electrode structure 110, and are placed in the same positions as sutures. A suture needle is brought through the tissue to the location of the U-clip (on the end). The surgeon cuts the suture thread at the end nearest the U-clip and the U-clip assumes the deployed position. In some embodiments, an "off the shelf" U-clip as described above may have to be modified to use the correct number of connection points and to be the correct size and shape (such as by making them circular) to match backer 114.

In a further embodiment depicted in FIGS. 10A-10E, fixation of electrode structure 110 is accomplished in whole or in part with the use of adhesives. Backer 114 may include one or more features to facilitate application of an adhesive, such as apertures 182, troughs 184, and/or tabs 186. Backer 114 may further include a perforated polyester mesh 188 strategically exposed to provide additional surface area to mate with the adhesive. Suitable adhesives include known medical adhesives such as Cryolife bioglue, acrylic-based adhesives or photo-activated adhesives. Anti-inflammatory and/or anti-scarring agents may be used in conjunction with an adhesive. Further, adhesive fixation be used in combination with other fixation means described herein.

Figure 11A:
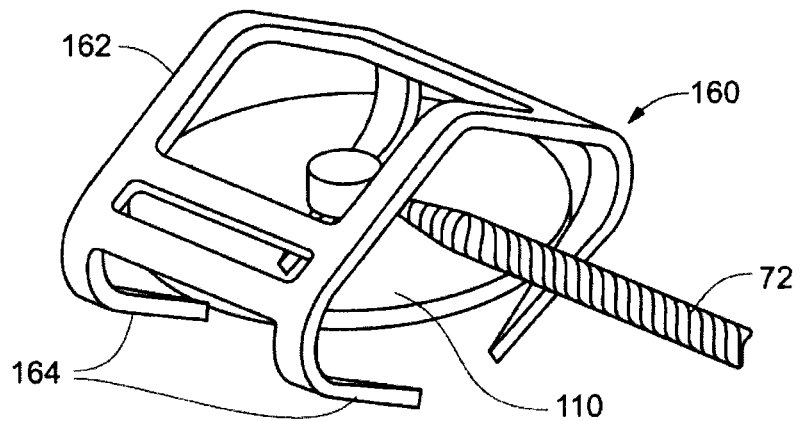
FIG. 11A is an isometric view of an electrode structure and fixation mechanism according to an embodiment of the present invention.
Figure 11B:
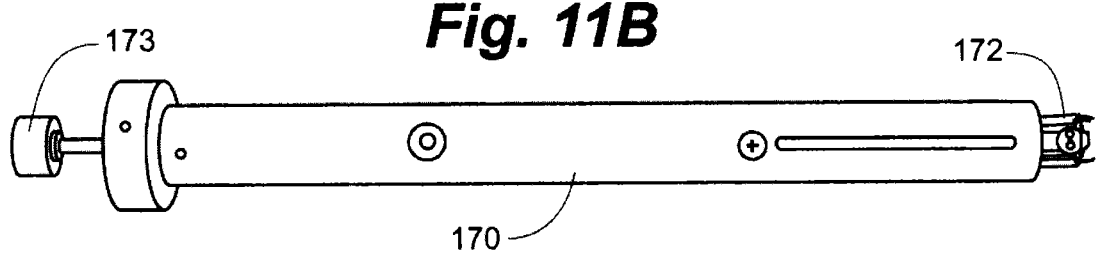
FIG. 11B is an elevation view of an implant tool according to another embodiment of the present invention for use with the electrode arrangement of FIG. 11A.
Figure 11C:
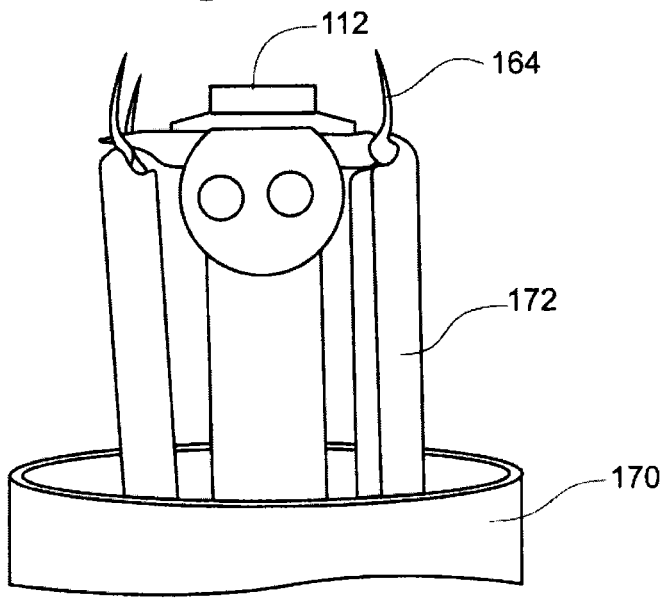
FIG. 11C is a close-up plan view of the electrode structure of FIG. 11A held in an open, retracted position by the implant tool of FIG. 11B.

In another embodiment depicted in FIGS. 11A-11C, electrode structure 110 includes an integrated, selectively deployable active fixation element 160 which generally includes a frame portion 162 and a plurality of fixation barbs 164. Fixation element 160 is coupled to electrode structure 110, and may be constructed of shape-memory alloy such as nitinol, or other suitable materials. An implant tool 170 is provided for mapping and implant of electrode structure 110, and generally includes a body portion 171 having a grasping means 172 at a distal end and a control means 173 at a proximal end. Control means 173 may be manipulated by a surgeon to cause grasping means 172 to hold frame portion 162 in a retracted position wherein fixation barbs 164 are retracted, thereby allowing introduction of electrode structure 110 to the implant site. A mapping procedure as described above may be carried out, and upon finding a satisfactory implant location, control means 173 is manipulated to cause grasping means 172 to release frame 162 and move fixation element 160 to a deployed position, allowing barbs 164 to penetrate into the adventitia of a blood vessel and securing electrode structure 110.

Figure 12A:
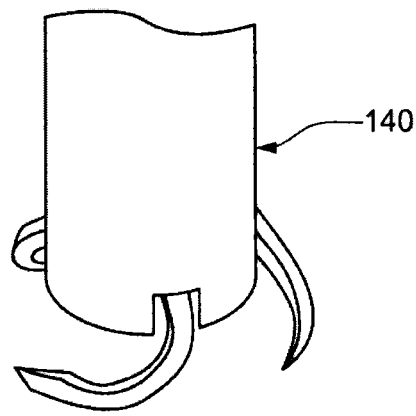
FIG. 12A is a perspective view of an implant tool according to another embodiment of the present invention.
Figure 12B:
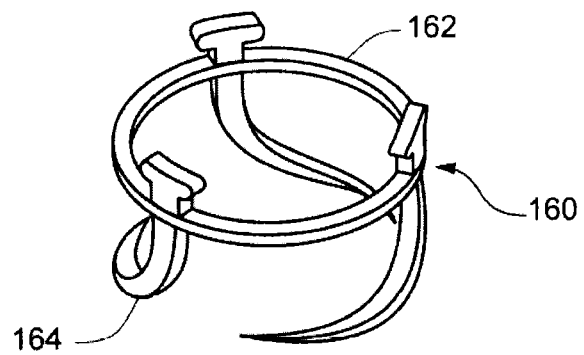
FIG. 12B is a perspective view of a fixation element for use with an electrode structure according to an embodiment of the present invention.

In an alternate embodiment depicted in FIGS. 12A-12B, fixation element 160 is deployed via a rotational approach. A plurality of barbs 164 are included on a frame 162, which is coupled to an electrode structure 110. Barbs 164 may be pre-formed to have a helix-like curvature. When retained by implant tool 140, barbs 164 are withdrawn into implant tool 140 or otherwise held in a retracted position as to allow for introduction of electrode structure 110 to the implant site and for mapping. When desired, implant tool 140 is manipulated to cause grasping means to rotatably deploy fixation element 162.

Referring now to operation of a baroreflex therapy system according to the present invention, as mentioned above the control signal generated by the control system 60 may be continuous, periodic, episodic or a combination thereof, as dictated by an algorithm contained in memory 62. The algorithm contained in memory 62 defines a stimulus regimen which dictates the characteristics of the control signal as a function of time, and thus dictates the stimulation of baroreceptors as a function of time. Continuous control signals include a pulse, a train of pulses, a triggered pulse and a triggered train of pulses, all of which are generated continuously.

The output (power or energy) level of the baroreceptor activation device 70 may be altered by changing the voltage, current and/or signal duration. The output signal of the baroreceptor activation device 70 may be, for example, constant current or constant voltage. In electrical activation embodiments using a modulated signal, wherein the output signal comprises, for example, a series of pulses, several pulse characteristics may be changed individually or in combination to change the power or energy level of the output signal. Such pulse characteristics include, but are not limited to: pulse amplitude (PA), pulse frequency (PF), pulse width or duration (PW), pulse waveform (square, triangular, sinusoidal, etc.), pulse polarity (for bipolar electrodes) and pulse phase (monophasic, biphasic).

In electrical activation embodiments wherein the output signal comprises a pulse train, several other signal characteristics may be changed in addition to the pulse characteristics described above. The control or output signal may comprise a pulse train which generally includes a series of pulses occurring in bursts. Pulse train characteristics which may be changed include, but are not limited to: burst amplitude (equal to pulse amplitude if constant within burst packet), burst waveform (i.e., pulse amplitude variation within burst packet), burst frequency (BF), and burst width or duration (BW). The signal or a portion thereof (e.g., burst within the pulse train) may be triggered by any of the events discussed previously, or by a particular portion of the arterial pressure signal or the ECG signal (e.g., R-wave), or another physiologic timing indicator. If the signal or a portion thereof is triggered, the triggering event may be changed and/or the delay from the triggering event may be changed.

Control signal characteristics for a baroreflex therapy system having a monpolar electrode 110 according to the present invention differ from prior approaches, and provide greater stimulation efficacy with a lower power consumption. For example, suitable pulse widths for the present invention are in the range of about 15 microseconds to 500 microseconds, preferably in the range of 60-200 microseconds, and more preferably in the range of 100-150 microseconds. Suitable pulse amplitudes are in the range of about 0.4-20 milliamps, preferably in the range of 3-10 milliamps, and more preferably in the range of 5-7 milliamps. Suitable pulse frequencies are in the range of about 10-100 Hz, preferably in the range of 25-80 Hz, and more preferably in the range of 40-70 Hz.

Figures 13A, 13B:
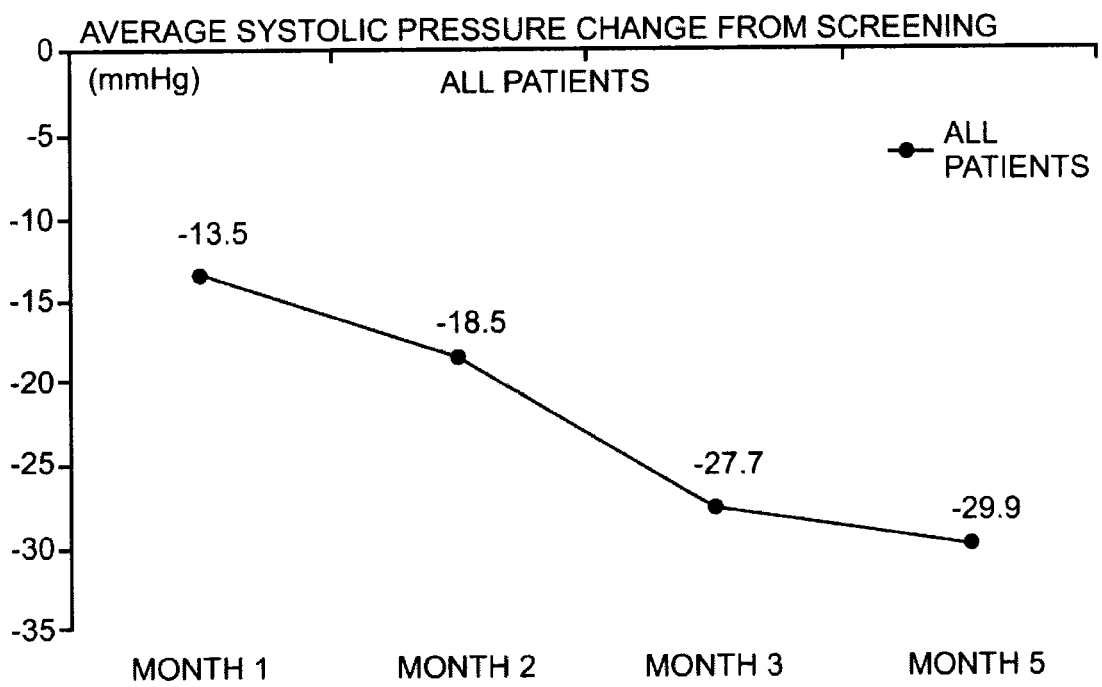
FIG. 13A is a table of operating parameters during an experiment described herein.
FIG. 13B is a graph depicting the results of the experiment described herein.

A number of human patients were implanted with baroreflex activation therapy systems according to the embodiments described herein. These patients had systolic blood pressures in excess of 140 mmHg despite the usage of at least three anti-hypertensive medications. The results of their first five months being implanted with the system are presented in FIGS. 13A-13B, which depict the average operating parameters for the system and the average resulting blood pressure reduction. These results illustrate that therapy delivered in accordance with the embodiments described herein resulted in a significant reduction in blood pressure of the patient.

Figure 14:
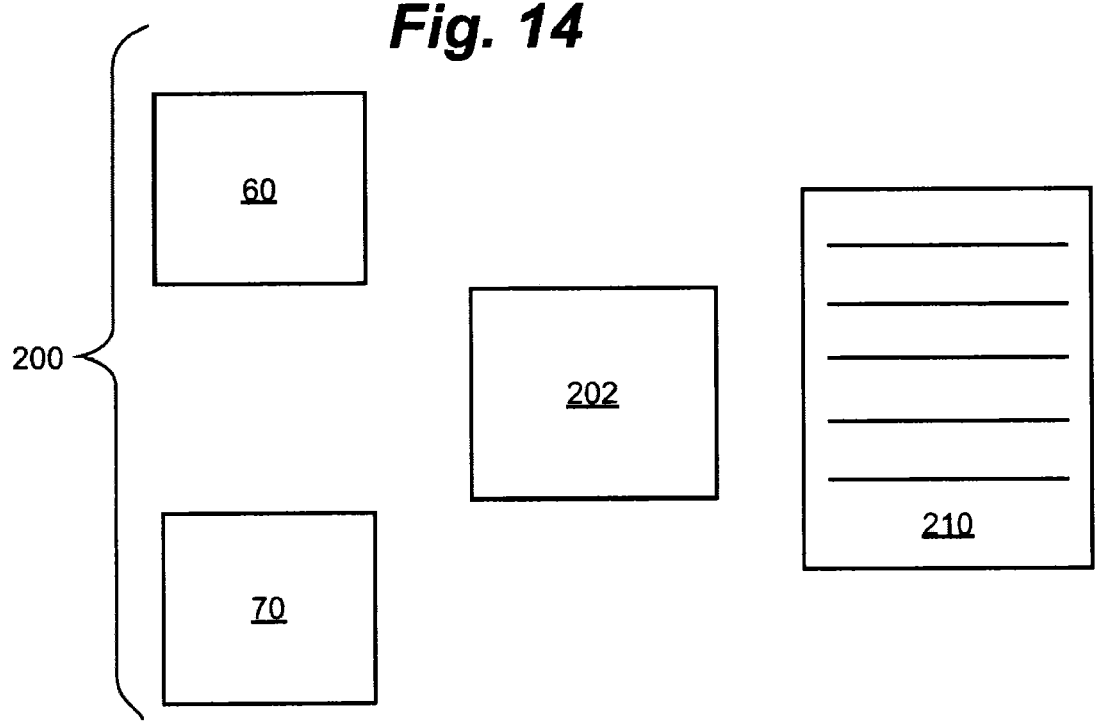
FIG. 14 is a schematic representation of a kit according to an embodiment of the present invention.

Referring now to FIG. 14, in one embodiment a baroreflex therapy system can be provided to a user in a kit 200. Kit 200 may include a control system 60 in a housing, a baroreflex activation device 70 having at least one electrode structure 110 and coupled to the control system, an optional sensor, an optional implant tool 202, and a set of instructions 210 recorded on a tangible medium for implanting, programming and/or operating the system. Kit 200 may be comprised of one or more hermetically sealed and sterilized packages. Instructions 210 may be provided as part of kit 200, or indications may be provided linking a user to electrically accessible instructions 210. Instructions 210 may include instructions for implanting electrode structure 110 and the baroreflex activation therapy system as described herein including the use of an implant tool and/or a mapping procedure, and/or for programming and/or operating control system 60.

Various modifications to the embodiments of the inventions may be apparent to one of skill in the art upon reading this disclosure. For example, persons of ordinary skill in the relevant art will recognize that the various features described for the different embodiments of the inventions can be suitably combined, un-combined, and re-combined with other features, alone, or in different combinations, within the spirit of the invention. Likewise, the various features described above should all be regarded as example embodiments, rather than limitations to the scope or spirit of the inventions. Therefore, the above is not contemplated to limit the scope of the present inventions.

Persons of ordinary skill in the relevant arts will recognize that the inventions may comprise fewer features than illustrated in any individual embodiment described above. The embodiments described herein are not meant to be an exhaustive presentation of the ways in which the various features of the inventions may be combined. Accordingly, the embodiments are not mutually exclusive combinations of features; rather, the inventions may comprise a combination of different individual features selected from different individual embodiments, as understood by persons of ordinary skill in the art.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the embodiments of the present inventions, it is expressly intended that the provisions of Section 112, sixth paragraph of 35 U.S.C. are not to be invoked unless the specific terms "means for" or "step for" are recited in a claim.

The invention claimed is:

1. An electrode structure for use in a baroreflex activation system to deliver baroreflex therapy to a baroreceptor within a wall of a blood vessel, the electrode structure configured for extravascular implantation, the electrode structure comprising:
   a backing material including an active side configured to be oriented toward a blood vessel, and an inactive side opposite the active side;
   an electrode arranged on the active side of the backing material; and
   an interface means arranged on the inactive side of the backing material, the interface means including a bar portion raised above the inactive side,
   wherein the interface means is configured for releasably coupling with a cradle of an implant tool, the cradle arranged at a distal end of the implant tool and including a pair of c-shaped hook portions.

2. The electrode structure of claim 1, wherein the backing material has a maximum linear dimension not greater than ten millimeters.

3. The electrode structure of claim 1, wherein the electrode structure is sized and configured to extend around less than half of a circumference of the blood vessel when implanted.

4. The electrode structure of claim 1, wherein an area of the backing material is at least ten times greater than an area of the electrode.

5. The electrode structure of claim 1, wherein an area of the backing material is at least thirty times greater than an area of the electrode.

6. The electrode structure of claim 1, further comprising a mesh layer disposed between the active side and the inactive side.

7. The electrode structure of claim 1, wherein the electrode is configured to be placed in contact with the blood vessel when implanted.

\* \* \* \* \*